United States Patent
Amirkhanian et al.

(10) Patent No.: US 8,114,349 B2
(45) Date of Patent: Feb. 14, 2012

(54) BIO-ANALYSIS CARTRIDGE TRACKING AND PROTECTION MECHANISM

(75) Inventors: Varouj Amirkhanian, La Crescenta, CA (US); Ming-Sun Liu, Brea, CA (US); Paul Mooney, Rancho Santa Margarita, CA (US)

(73) Assignee: Qiagen Sciences, LLC, Germantown, MD (US)

( * ) Notice: Subject to any disclaimer, the term of this patent is extended or adjusted under 35 U.S.C. 154(b) by 2215 days.

(21) Appl. No.: 11/022,313

(22) Filed: Dec. 23, 2004

(65) Prior Publication Data

US 2005/0189219 A1 Sep. 1, 2005

Related U.S. Application Data

(63) Continuation-in-part of application No. 10/319,803, filed on Dec. 13, 2002, now Pat. No. 7,250,099, and a continuation-in-part of application No. 10/059,993, filed on Jan. 28, 2002, now Pat. No. 7,309,409, and a continuation-in-part of application No. 10/973,828, filed on Oct. 25, 2004, now Pat. No. 7,846,315, and a continuation-in-part of application No. PCT/US03/39971, filed on Dec. 15, 2003, and a continuation-in-part of application No. 10/823,382, filed on Apr. 12, 2004, now Pat. No. 7,622,083.

(60) Provisional application No. 60/532,671, filed on Dec. 23, 2003.

(51) Int. Cl.
*G01N 15/06* (2006.01)
*B01D 57/02* (2006.01)
*B01D 15/08* (2006.01)

(52) U.S. Cl. ....... 422/68.1; 422/400; 422/417; 204/450; 204/451; 204/456; 210/198.2; 210/656; 356/344

(58) Field of Classification Search .................. None
See application file for complete search history.

(56) References Cited

U.S. PATENT DOCUMENTS 4,782,949 A * 11/1988 Berkman ................. 206/387.14
(Continued)

FOREIGN PATENT DOCUMENTS

EP 0021499 1/1981
(Continued)

OTHER PUBLICATIONS

Partial International Search Report of Counterpart PCT Application No. PCT/US2004/043424.

*Primary Examiner* — Jill Warden
*Assistant Examiner* — Neil N Turk
(74) *Attorney, Agent, or Firm* — Liu & Liu

(57) ABSTRACT

A reusable bio-analysis cartridge that includes a built-in mechanism to track various parameters and usage data. The tracking mechanism includes a non-volatile rewritable memory "smart-key" that is associated with the cartridge to provide automatic tracking dedicated to the cartridge. The key may be physically coupled to the cartridge with good high voltage insulating properties. When the cartridge is used in an instrument, the associated key is inserted into an I/O interface to communicate with the instrument. The instrument may be configured to "authenticate" the cartridge and conduct an integrity check to determine if the particular cartridge has the correct properties (e.g., gel-chemistry, serial no., Patient I.D.) for the particular sample analysis to be conducted. Further, the instrument may communicate/record information concerning usage of the cartridge (e.g., usage history, test parameters, and perhaps test results). Such information provides an update to the stored information from the previous use of the cartridge.

16 Claims, 8 Drawing Sheets

U.S. PATENT DOCUMENTS

| | | | | |
|---|---|---|---|---|
| 4,985,129 | A | * | 1/1991 | Burd .............................. 204/603 |
| 5,037,523 | A | * | 8/1991 | Weinberger et al. .......... 204/602 |
| 5,524,749 | A | * | 6/1996 | Thompson et al. ............. 206/38 |
| 6,484,937 | B1 | * | 11/2002 | Devaux et al. ................. 235/380 |
| 6,602,469 | B1 | * | 8/2003 | Maus et al. .................. 422/68.1 |
| 6,613,224 | B1 | * | 9/2003 | Strand ........................ 210/198.2 |

FOREIGN PATENT DOCUMENTS

| | | |
|---|---|---|
| WO | WO 02/28509 | 4/2002 |
| WO | WO 02/059589 | 8/2002 |

* cited by examiner

BIO-ANALYSIS CARTRIDGE TRACKING AND PROTECTION MECHANISM

This application claims the priority of U.S. Provisional Patent Application No. 60/532,671, filed on Dec. 23, 2003. This Provisional Patent Application is fully incorporated by reference herein, as if fully set forth herein.

This application is a Continuation-in-Part of the following U.S. patent applications: U.S. patent application Ser. No. 10/059,993 entitled "Multi-Channel Bio-Separation Cartridge," filed on Jan. 28, 2002 now U.S. Pat. No. 7,309,409; U.S. patent application Ser. No. 10/973,828, entitled "Integrated Bio-Analysis and Sample Preparation System", filed on Oct. 25, 2004 U.S. Pat. No. 7,846,315; U.S. patent application Ser. No. 10/319,803, entitled "Optical Detection Alignment Coupling Apparatus", filed on Dec. 13, 2002 now U.S. Pat. No. 7,250,099; and PCT Application No. PCT/US03/39971, entitled "Optical Detection Alignment Coupling Apparatus", filed on Dec. 15, 2003; and U.S. patent application Ser. No. 10/823,382, entitled "Multi-Capillary Electrophoresis Cartridge Interface Mechanism", filed on Apr. 12, 2004 now U.S. Pat. No. 7,622,083, which are all commonly assigned to BioCal Technology, Inc., the assignee of the present invention.

The present invention also relates to U.S. Pat. No. 6,828,567, which has been commonly assigned to Biocal Technology, Inc., the assignee of the present invention.

The above-mentioned applications, and all other applications, patents, documents and references noted in the disclosure herein below, are fully incorporated by reference as if fully set forth herein.

BACKGROUND OF THE INVENTION

1. Field of the Invention

The present invention relates to a reusable specimen cartridge for use in a bio-analysis system, and particularly a bio-analysis cartridge that includes a tracking mechanism and protection mechanism for its contents, and more particularly to a capillary electrophoresis cartridge having such tracking mechanism and content protection mechanism.

2. Description of Related Art

Bio-analysis, such as DNA analysis, is rapidly making the transition from a purely scientific quest for accuracy to a routine procedure with increased and proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to ease sample handling during the process, and in general, to have a simplified, low cost, high sensitivity detector.

One type of DNA analysis instrument separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules that have equivalent charge-to-mass ratios but different masses. DNA fragments are one example of such molecules.

There are a variety of commercially available instruments applying electrophoresis to analyze DNA samples. One such type is a capillary electrophoresis (CE) instrument. By applying electrophoresis in a fused silica capillary column carrying a separation support medium (e.g., a buffer solution, a gel matrix having a particular gel-chemistry), the sample size requirement is significantly smaller and the speed of separation and resolution can be increased multiple times compared to the slab gel-electrophoresis method. These DNA fragments in CE are often detected by directing light through the capillary wall, at the components separating from the sample that has been tagged with a fluorescence material, and detecting the fluorescence emissions induced by the incident light or by means of absorbance detection techniques. In fluorescence type detection the intensities of the emission are representative of the concentration, amount and/or size of the components of the sample. In the past, Laser-induced fluorescence (LIF) detection methods had been developed for CE instruments. Fluorescence detection is often the detection method of choice in the fields of genomics and proteomics because of its outstanding sensitivity compared to other detection methods.

The capillary column may be a part of a removable cartridge that can be separated from the system for storage, transport or reuse. Because different cartridge may be pre-assembled with different content, for example, a different gel-chemistry, the content of the cartridge should be identified. Visual indicators may be provided to identify the cartridge and its contents. For example, a label (e.g., with a bar-code) or separate information sheet may be applied to the cartridge. In addition, in view of the reusability of the cartridge and defined usage or shelf life of the contents of the cartridge, a separate log may be associated with the particular cartridge for keeping track of the usage of the cartridge. However, a label only contains information at the time the label was placed on the cartridge. A separate information sheet could easily be misplaced or mismatched to different cartridge of different gel-chemistry, for example. Any update in the information much be applied manually by a user, such as by writing on the cartridge or reapplying a label, or maintaining accurate records in the separate log. In the laboratory environment, where important bio-analysis is being conducted (such as clinical diagnostics type applications, where FDA mandates proper record keeping steps i.e. patient record/info tracking), the manual step of keep track of updating or logging of information would present a potential for errors and omissions. It is therefore desirable to have a reusable capillary cartridge for use with a CE instrument that includes a mechanism to automatically track information associated with a particular cartridge.

The cartridge is pre-assembled with capillaries filled with a separation support medium the property of which may potentially deteriorate with prolonged exposure to the environment. Given that the reusable cartridge may be stored in-between use, the separation support medium exposed at the tip of the capillaries would be most likely to deteriorate, such as drying of a gel matrix, causing blockage of the capillaries and creating issues when the cartridge is reused. It would be desirable to improve the life of the cartridge and its contents during storage.

SUMMARY OF THE INVENTION

The present invention provides a reusable, interchangeable cartridge for use in a bio-analysis system that includes a built-in mechanism to reliably track various parameters and data, and further a means to protect its content from damage and drying. The present invention also provides a bio-analysis instrument with an interface that supports the tracking mechanism of the reusable cartridge.

In one aspect of the present invention, the reusable cartridge includes a tracking mechanism to store relevant data relating to the cartridge and its attributes, such as content and usage. The cartridge is portable, recyclable, reusable and interchangeable with other cartridges having different types of channels (e.g., separation medium, channel size, internal wall coating, etc.). It defines a separation channel, which may be a capillary supported in the cartridge or a micro-column defined in the cartridge. In one embodiment of the present invention, the tracking mechanism includes a non-volatile rewritable memory "smart key" (e.g., comprising a EEPROM) that is associated with the cartridge to provide automatic tracking dedicated to the cartridge. The key may be physically coupled to the cartridge (e.g., attached to the body of the cartridge or by a tether), or separate from the cartridge. When the cartridge is used in an instrument, the associated key is inserted into a data interface (e.g., a reader/writer) in the instrument to communicate with the instrument the relevant information concerning the cartridge and it content. The instrument may be configured to "authenticate" the cartridge and conduct an integrity check to determine if the particular cartridge has the correct properties (e.g., gel-chemistry) for the particular sample analysis to be conducted. Further, the instrument may communicate/record information concerning usage of the cartridge (e.g., how and when the cartridge had been used, usage history or number of runs, test parameters, and perhaps test results). Such information provides an update to the stored information from the previous use of the cartridge.

In another aspect of the present invention, a modular cartridge interface that is a part of a dedicated bio-analysis instrument is provided. In one embodiment of the present invention, the modular cartridge interface consists of a cartridge-mating interface and an Input/Output (I/O) port. The modular interface is a part of a portable bio-analysis system, for example, designed for a single or multi-capillary cartridge that is used in CE analysis. Yet in another embodiment, the bio-analysis instrument reads and writes data with respect to the tracking device of the cartridge in connection with the operation of the instrument.

In a further aspect of the present invention, the fragile capillary tips of a capillary cartridge are kept from being damage. In one embodiment, a cartridge stand is provided to keep the capillary cartridge in an upright or vertical position while its capillary tips are immersed in a compatible material designed to keep the content of the tips from drying. In another embodiment, a packaging container and tip cushions/protectors are provided to protect the cartridge and its content from damage and drying during storage and transport.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF ILLUSTRATED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides a reusable capillary cartridge for use in a bio-analysis system that includes a built-in mechanism to reliably track various parameters and data, and further a means to protect its content from damage and drying. The present invention also provides a bio-analysis instrument with an interface that supports the tracking mechanism of the reusable cartridge. In one aspect of the present invention, the reusable cartridge includes a tracking mechanism to store relevant data relating to the cartridge and its content and usage. In another aspect of the present invention, a modular cartridge interface that is a part of a dedicated bio-analysis instrument is provided. In a further aspect of the present invention, the fragile capillary tips of a capillary cartridge are kept from being damage.

For purpose of illustrating the principles of the present invention and not by limitation, the present invention is described by reference to embodiments directed to CE analysis. In the illustrated embodiment, the invention provides a tracking mechanism (a data key) for a reusable CE cartridge supported by an integrated and automated multi-channel CE system.

BioCal Technology, Inc., the assignee of the present invention, developed a CE-based automated instrument (e.g., Model HDA-GT12 DNA Analyzer System). The illustrated embodiment of the automated instrument is based on BioCal's CE instrument, which incorporates an interface for supporting the tracking key, along with low-cost and sensitive optical detection technology, integrated reagents cartridge and micro-fluidic electrophoresis principle for a real-time fluorescent analysis, to form a sensitive and accurate bioagent detection (genetic analysis) system. The system is designed to be high-throughput, easy-to-use, portable, inexpensive, very robust and for field operation/applications.

The cartridge developed by BioCal (e.g., Model GC-5000 or GC-10K) is designed to be supported by the instrument, with all essential cartridge elements aligned and coupled to support elements in the instrument. The cartridge is held with respect to sample trays that can be moved in relation to the capillary separation channels in the cartridge. The tracking data key can be inserted into a reader/writer in the instrument.

Overview of CE System

Figure 1:
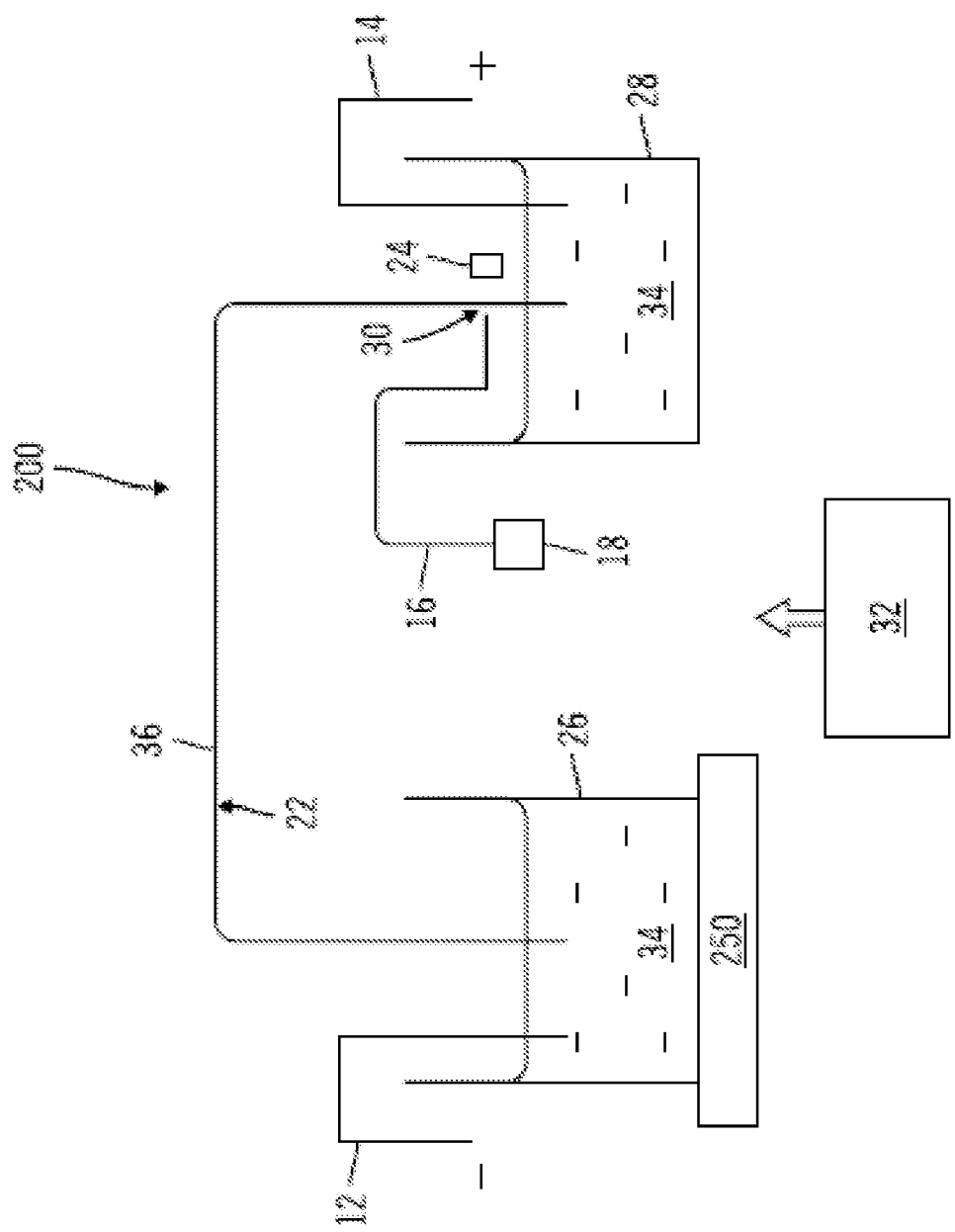
FIG. 1 is a schematic representation view of a capillary electrophoresis system that comprises a sample preparation device in accordance with one embodiment of the present invention.

FIG. 1 is a schematic representation of a capillary electrophoresis (CE) system 200 in accordance with one embodiment of the present invention. The CE system 200 generally comprises a capillary separation column 22 (e.g., 200-500 µm O.D.), which defines a separation channel 36 (e.g., 25-200 µm I.D.). The capillary column 22 may be made of fused silica, glass, polyimide, or other plastic/ceramic/glassy materials. The inside walls of the separation column 22 (i.e., the walls of the separation channel 36) may be coated with a material that can build up an electrostatic charge to facilitate electrophoresis and/or electrokinetic migration of the sample components. The separation channel 36 is filled with a separation support medium, which may be a running buffer, or in the illustrated embodiment a sieving gel matrix known in the art. For radiation induced fluorescence detection, the gel matrix includes a known fluorophore, such as Ethidium Bromide.

One end of the capillary column 22 is submerged in a reservoir 28 of running buffer/gel 34. The other end of the capillary column 22 is coupled to the sample vial 26. It is understood that other detection configurations implemented in a system similar to the CE system 200. A radiation detector 24 is positioned outside a transparent section of the capillary walls at detection zone 30. An excitation fiber 16 extends from a radiation source 18 (e.g., LED or laser) and is directed at the detection zone 30 outside the walls of the column. Electrodes 12 and 14, that are part of the cartridge assembly are coupled to the buffer reservoirs 26 and gel reservoir 28 to complete the electrophoresis path.

Overview of CE Separation and Analysis

In operation, a prepared biological sample (e.g., a DNA/RNA sample) in the sample vial 26 is introduced into the far end of the capillary column 22 away from the detection zone 30 by any of a number of ways (e.g., electrokinetic injection from the sample reservoir). The sample binds to the fluorophore in the gel matrix supported in the capillary column 22.

When a DC potential (e.g., 1-30 KV) is applied between electrodes 12 and 14, the sample migrates under the applied electric potential along the separation channel 36 (e.g. DNA that is negatively charged travels through the sieving gel with an integrated dye matrix/fluorophore toward a positive electrode as shown in FIG. 1) and separates into bands of sample components (DNA fragments). The extent of separation and distance moved along the separation channel 36 depends on a number of factors, such as migration mobility of the sample components, the mass and size or length of the sample components, and the separation support medium. The driving forces in the separation channel 36 for the separation of samples could be electrophoretic, pressure, or electro-osmotic flow (EOF) means.

When the sample reaches the detection zone, excitation radiation is directed via the excitation fiber 16 at the detection zone. The sample components fluoresce with intensities proportional to the concentrations of the respective sample components (proportional to the amount of fluorescent tag material). The detector 24 detects the intensities of the emitted fluorescence at a wavelength different from that of the incident radiation. The detected emitted radiation may be analyzed by known methods. For the automated system, a controller 32 (discussed below in connection with FIG. 5) on the electronic board 64 (FIG. 4) controls the operations of the CE system 200.

Capillary Cartridge with Tracking Data Key

Figure 2:
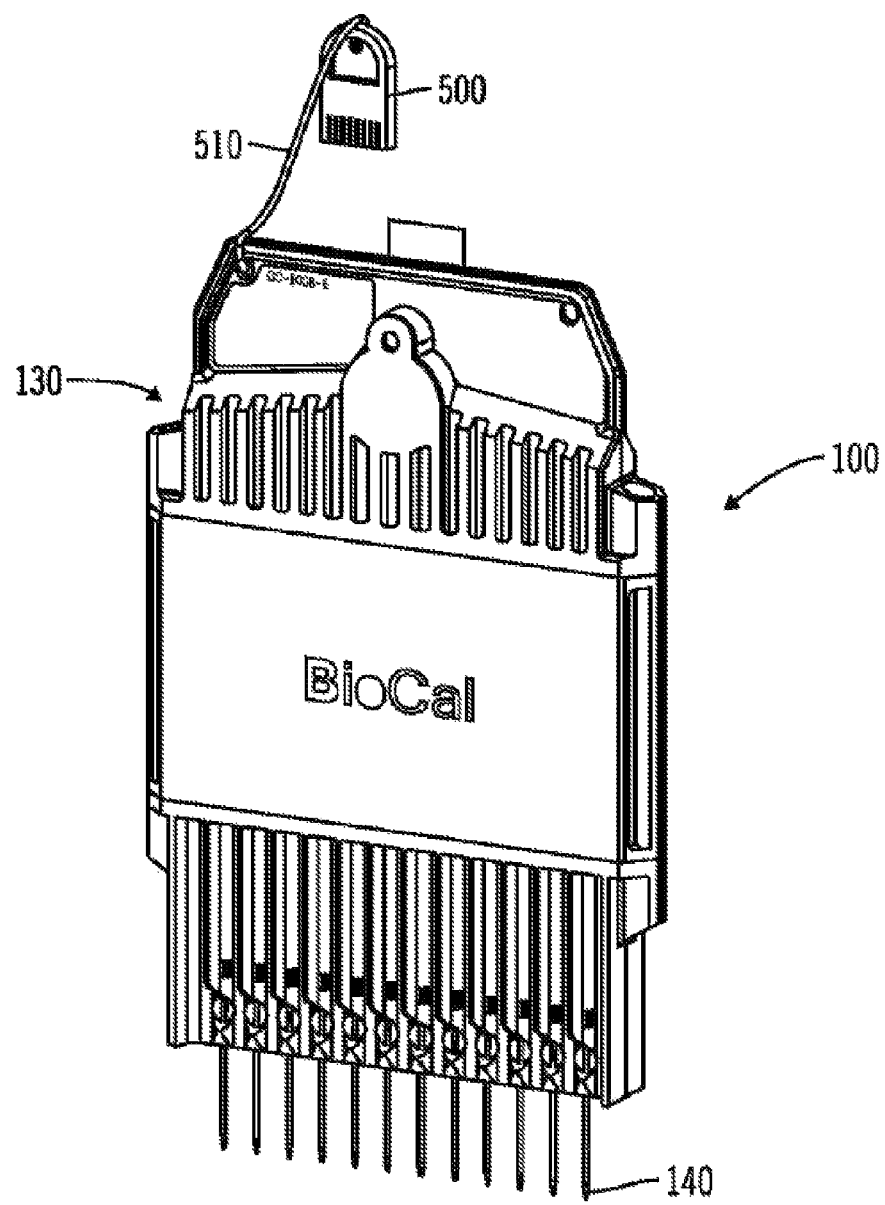
FIG. 2 is a perspective view of a capillary cartridge having a tracking device in accordance with one embodiment of the present invention.

FIG. 2 is a perspective view of the CE cartridge having a tracking data key in accordance with one embodiment of the present invention.

The multi-channel capillary cartridge 200 includes twelve detection zones (schematically represented as 30 in FIG. 1), defined by capillaries 140 held in a cartridge body. A data key 500 is associated with the cartridge 100 (e.g., by a tether or cord 510 as shown). Details relating to the data key 500 will be discussed later below. The cartridge 100 includes a twelve-channel fused silica capillary array that is used for separation and detection of the samples as part of a disposable and/or portable, interchangeable cartridge assembly 100. The cartridge 100 shown in FIG. 2 holds up to 12 capillaries 140, 12-18 cm long. The cartridge 100 is integrated with a top, outlet buffer reservoir 130 common to all capillaries 140, which is directly coupled by the interface mechanism 300 to a modular compressed gas source 78, such as a replaceable pressurized gas cartridge of an inert, compatible or non-reactive gas (e.g., Nitrogen, compressed air, $CO_2$, etc.) or a pressure pump. Appropriate pressure plumbing, including tubing, pressure valve and solenoid controls, is provided. (Details of such plumbing are omitted, since it is well within one skilled in the art to configure such plumbing given the disclosure herein of the functions, features and operations of the system 200.) The pressure source 78 provides the required gas pressure to fill-up all the 12-capillaries with the sieving gel contained in the reservoir 130 and to purge the gel from the previous run from the capillaries during the refilling process. Depending on the viscosity of the gel, pressures of up to 40 PSI may be applied to the capillaries 140 through the gel-filled reservoir 130.

The cartridge gel-reservoir 130 is equipped with a built in common electrode anode (not shown, but equivalent to anode 14 in FIG. 1) for all 12-capillaries, which is automatically connected by the interface mechanism 300 to the high voltage power supply 76 (FIG. 2) for electrophoresis when installed inside the system 200. A fan or Peltier cooler (not shown) on the adjacent structure to the cartridge 100 may be provided to provide temperature control of the cartridge. In addition or in the alternate, the cartridge may have vent holes (input and output) for air circulation (temperature controlled air to be introduced to the cartridge from the instrument side). Depending on the heat generated during CE separation, the cartridge may simply be exposed to ambient temperature, with no auxiliary cooling features.

Figure 3:
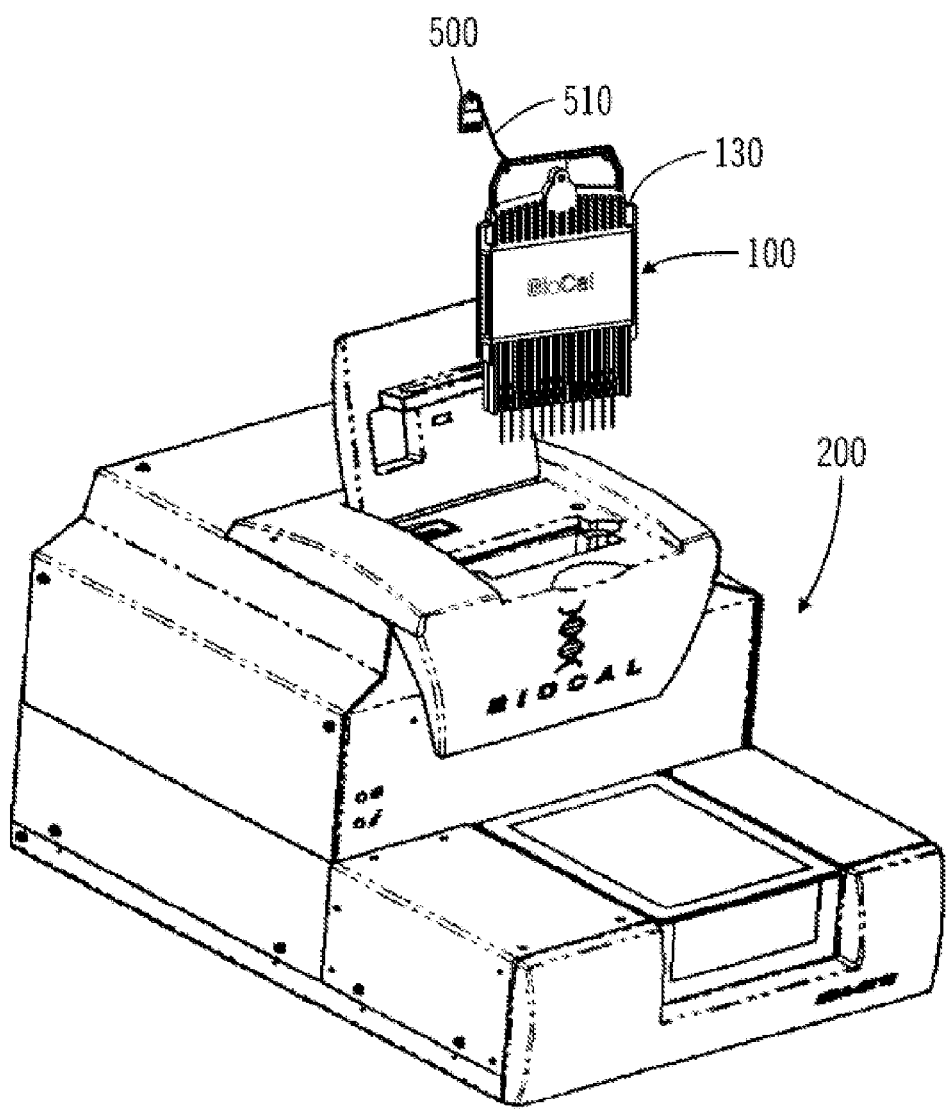
FIG. 3 is a perspective external view of a bio-analysis instrument that uses the capillary cartridge of FIG. 2, in accordance with one embodiment of the present invention.
Figure 4:
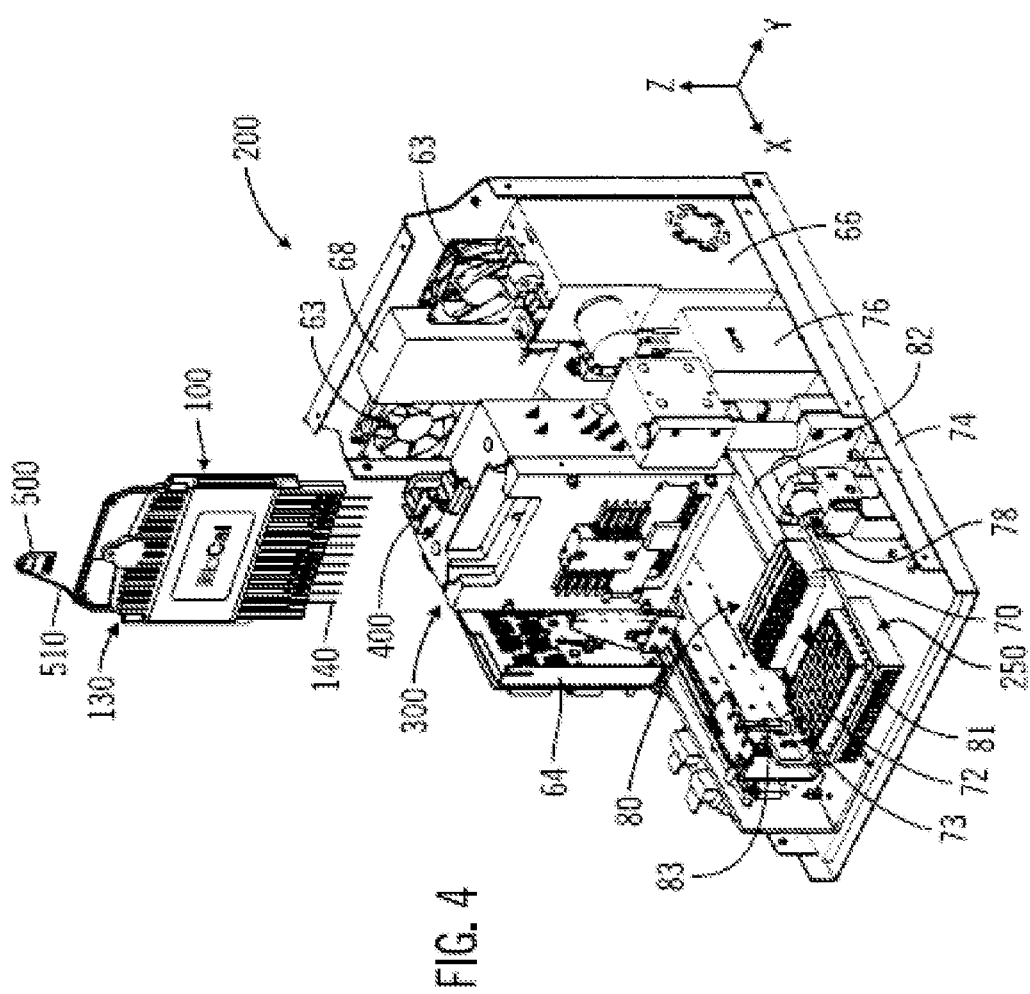
FIG. 4 is a perspective internal view of the bio-analysis instrument of FIG. 3, in accordance with one embodiment of the present invention.

In one embodiment, the cartridge 100 is received in the automated CE system 200 shown in FIGS. 3 and 4. A power supply 66 (FIG. 4) provides DC power to the CE system 200 to be supplied to the cartridge, as will be further explained below.

Further details of the cartridge may be referenced to the copending application Ser. No. 10/059,993, which had been fully incorporated by reference herein.

Data Key

According to an embodiment of the present invention, the capillary cartridge 100 includes a tracking mechanism that includes an EEPROM Serial Memory Key 500 that is attached by a tether or cord 510 to the capillary cartridge 100. This Serial Memory Key (e.g., produced by Datakey Electronics) is a portable data key that allows the storage and transport of data. Each of these devices comprises a non-volatile, serial Microwire™ EEPROM that can be read, erased and written to via an I/O port 400 located on the CE instrument 200 (FIG. 4). The key 500 is packaged to include the memory and appropriate conductive contacts or leads to interface with an external reader/writer at the I/O port 400

(discussed below in connection with FIG. 4). The data key 500 requires approximately +5 volt and operates through a direct connection with the I/O port 400 on the CE instrument 200. Other types of data key may be used instead, which may include magnetic recording memories, optical recording memories, etc.

A cord 510 is used to physically attach the data key 500 to the capillary cartridge 100 allowing any data residing on the data key 500 to be identified with the capillary cartridge 100. Yet, the cord 510 provides enough slack so that the data key 500 can be inserted into an I/O port 400 that is physically isolated and electrically protected from the cartridge-mating interface 300 (discussed below) to prevent any memory loss or corruption during the high voltage electrophoresis process. In an alternate embodiment, for cartridges designed for use in low-voltage instrument environments, the data key may be physically attached to the cartridge by bonding, or made a unitary or an integral part of the cartridge body. Further, while a tether is shown in the illustrated embodiment, for certain applications, the data key may be separate from the cartridge, as long as the data key can be associated with the cartridge by some way, e.g., by physical markings, labeling, etc.

In one embodiment, the data key 500 is used to retain data relating to the attributes, properties and/or configuration of the cartridge, including one or more of the following: model number, serial number, I.D. of patient/subject that cartridge is assigned to, type of cartridge (e.g., number of capillary channels, size of capillary channels, type of gel-chemistry), date of manufacturing, chemistry lot number, etc., and may include preprogrammed test protocols, specific design limitations, restriction or constraints concerning use of the cartridge (e.g., expiration date, maximum voltage, maximum number of runs, maximum hours of use, chemistry compatibility, instrument compatibility, method/sequence steps/settings associated with specific applications, test protocols, compatibility of other analysis parameters, authorized class of users, etc.), and any other data for use "initializing" the instrument and/or the cartridge when the cartridge is first used or a particular/specific pre-programmed method/sequence steps/function are called out by the reader/instrument. Preprogrammed test protocols may include programmed specific sequence/method steps (e.g., method=purge+pre-injection (washing solution)+DNA/sample injection+separation in buffer) with pre-programmed time and voltage intervals that can be readable by the instrument/software as the cartridge is connected for usage/analysis, which prevents it from misuse and/or abuse of the gel-cartridge by end users. Further it extends the life and the resolution quality/integrity of detected DNA fragments.

In another embodiment, the data key 500 is used to retain usage data that may be updated with each use. For example, data may be updated concerning one or more of the following: number of applied electrophoretic runs, types of runs, run I.D.'s, patient/subject I.D., run protocols, run conditions and parameters, dates of use, separate and cumulative run time, applied run voltage/current, instrument system ID's, user or patient ID, etc. By tracking usage, one (or the instrument 200) can determine the remaining life of the cartridge, by considering factors such as run time, run condition, etc. By storing system ID's, one can trace the usage of the cartridge, for example in the event of a problem recall on the cartridge, the runs conducted with the particular cartridge at various instruments can be determined quickly and the results of those runs can be audited to determine the effect of the problems with the cartridge on the analysis results or by having a patient I.D. one can easily track patient test data/results. If it is desirable to dedicate a particular cartridge for use in a particular instrument, the data key may be "lock" to only work with a particular instrument upon initial use. The "lock" code associated with the instrument can be stored in the data key.

In a further embodiment, the data key 500 may also store the results of all or some of the runs conducted.

The data key 500 may be read/written by the I/O port 510 on the instrument 200, or a dedicated reader/writer (not shown).

Cartridge Stand

Figure 6:
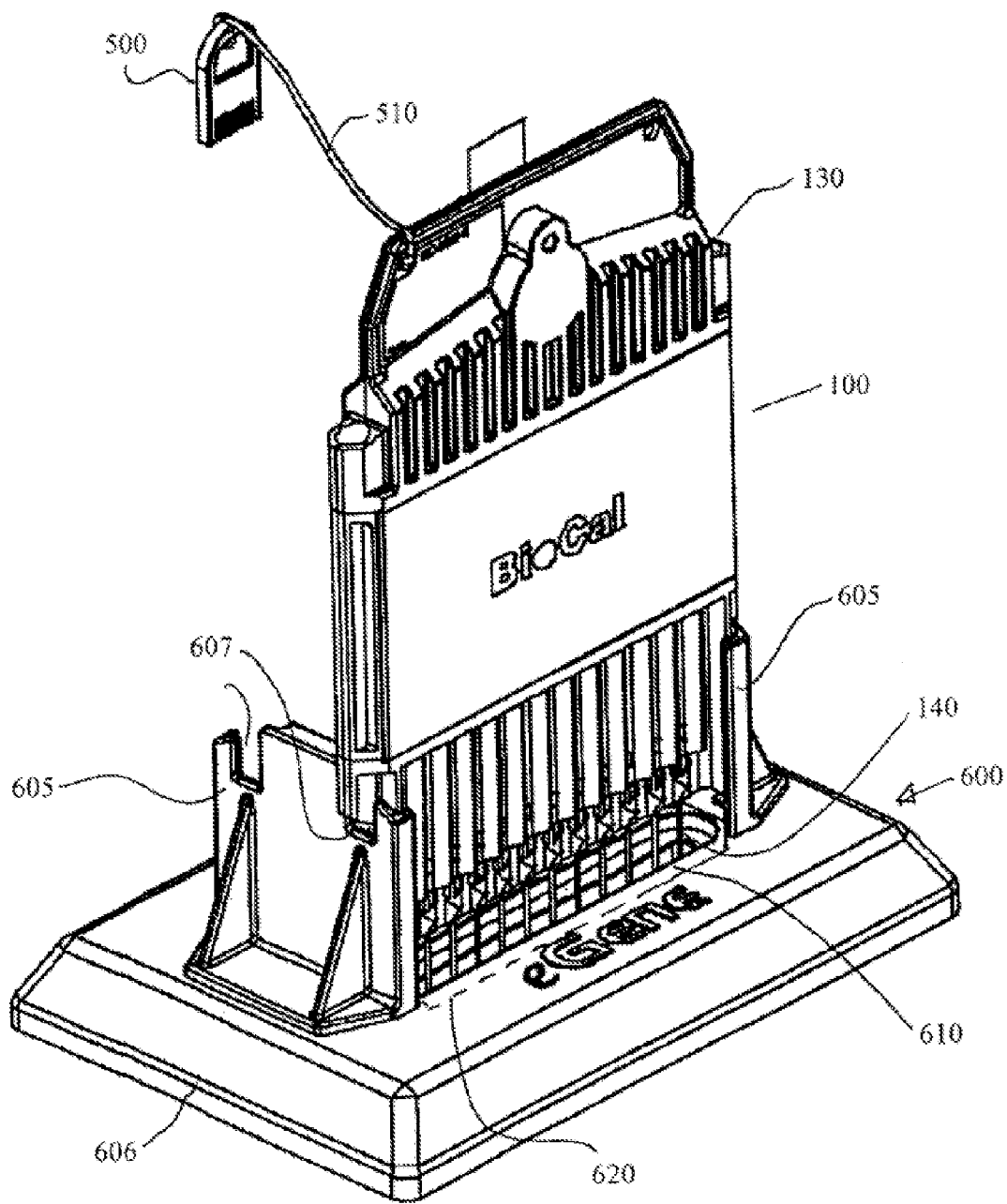
FIG. 6 is a perspective view of the capillary cartridge resting in its parking stand in accordance with one embodiment of the present invention.

FIG. 6 shows the capillary cartridge with the attached tracking mechanism resting in a capillary cartridge parking stand 600. The stand 600 includes two supports 605 on a base 606, having notches 607, sized and spaced apart to receive the cartridge 100. In the embodiment shown in FIG. 6, the stand 600 is designed to support two cartridges 100.

In one embodiment of the present invention, the parking stand 600 is designed to keep the cartridge 100 in an upright (vertical) position, which facilitates the gel-migrations within the micro-channels of the capillaries 140. Due to gravity feeding of the gel within the micro-channels, the capillary cartridge 100 is maintained in a prepared state ready for use in the bio-analysis system, by maintaining a stable and reliable operating condition of the capillaries. For example, the gel matrix would maintain filling of the coated capillaries 140, to preserve the integrity of the coating.

The parking stand 600 is designed with a micro-well liquid slot 610 at the bottom of the stand where the capillary tips and the surrounding electrodes are inserted while the cartridge 100 is in a parked position. The well 610 may be filled with BioCal's Washing Solution (Product number GCW-5000) or other liquid such as mineral oil to keep the capillary tips wet at all times, the gel matrix from drying. Alternatively, a paste, non-drying gel or thick oil type material may be used in the well 610. The material in the well 610 in the parking stand 600 is designed to have compatible chemical properties with the gel solution contained in the capillary cartridge 100.

Capillary Tip Sealing

Figure 7:
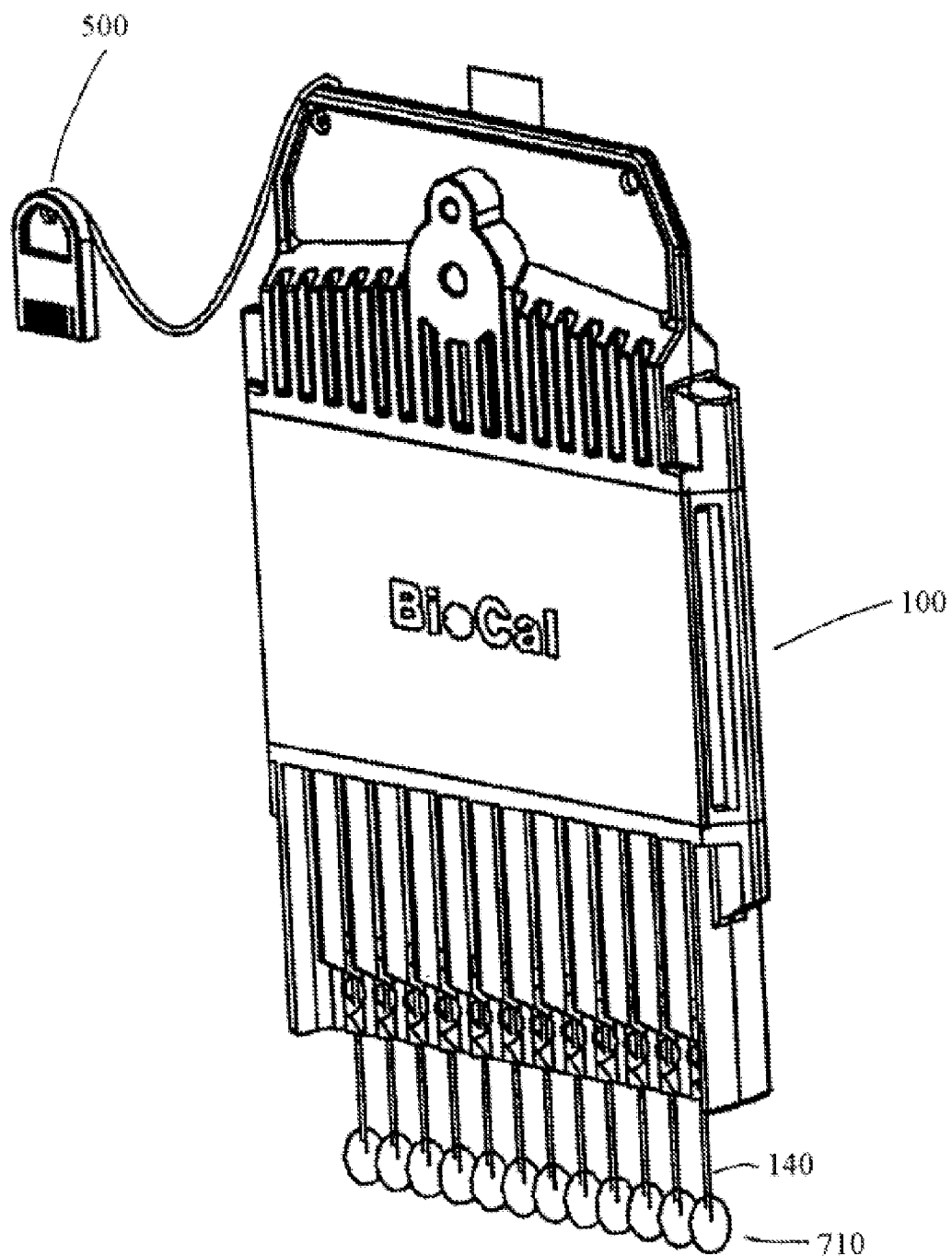
FIG. 7 is a perspective view of the capillary cartridge with its capillary tips inserted into protective caps in accordance with one embodiment of the present invention.

FIG. 7 is a perspective view of the capillary cartridge 100 with its capillary tips covered by protective caps 710 having a sealing material to protect the tips from premature drying. In one embodiment, the protective caps 710 have a capsule structure similar to a softgel capsule for medication, comprising a thin walled sealed capsule containing a sealing material. The capsule may be made of plastic or silicon material. The sealed/closed capsules of the caps 710 are filled with mineral oil or other gel-compatible solution or paste. To use the caps 710, a small hole may be made in the capsule with a piecing instrument such as a pin before inserting the capillary tip, or by directly piercing the capsule with the pointed tip of a capillary 140 to which it is to be attached. The elasticity of the thin walled capsule grips onto the capillary tip.

In an alternate embodiment, the protective caps 710 may comprise open capsules that are either filled or coated with a thick sealing material such as a gel-compatible paste or gel.

In a modified embodiment not shown, the caps 710 may be integrated in a single large one-piece capsule sealing cap, having separate capsule compartments corresponding to each capillary 140 in the cartridge 100, or a single elongated capsule covering all or groups of capillaries in the cartridge 100. Alternatively, the protective cap may be in the form of a trough or elongated well (similar to the well 610 in FIG. 6) that is filled with a compatible sealing material. In yet a further embodiment, the base 606 of the stand 600 can provide an opening that is sized to receive the elongated cap. In other words, in a modified embodiment of FIG. 6, a removable trough may be defined, as schematically shown by dotted line 620, which can be received in a compatible opening in the base of the stand 600. The cartridge 100 may be removed or placed on the stand 600 with the one-piece protective cap in place at the capillary tips.

Cartridge Transport Package

Figure 8:
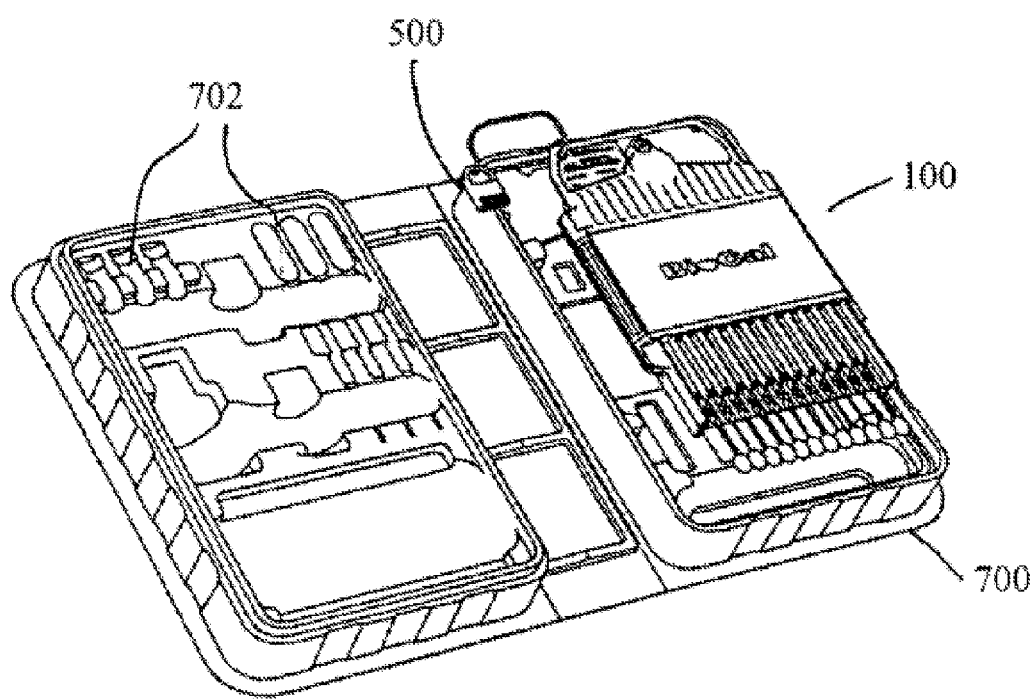
FIG. 8 is a perspective view of the capillary cartridge in its carrying case in accordance with one embodiment of the present invention.

For the storage and transport of the cartridge 100, the cartridge 100 with the protective caps shown in FIG. 7 may be further protected from physical hazards by enclosed in a protective case 700 as shown in FIG. 8. The case 700 can be made of molded rigid or semi-rigid plastic, such as ethylene, polyethylene, PVC, etc. At least one of the two halves of the case 700 are molded with a shape to complement the external shape of the cartridge 100, and the two halves are sized and shaped to be able to be closed upon each other in a clamshell fashion. Alternately or in addition, the case 700 may include pre-defined opening or wells 702 for receiving and/or holding items such as the data key 500, small tools, solution dispensing pipettes, DNA/Calibration Markers, micro-titer sample plates, reagent bottles, extra protective caps 710, other supplies, etc., that complements the use of the cartridge 100.

In a further embodiment not shown, the protective case 700 may contain a well (not shown) that is filled with a gel-compatible sealing material, so that when the cartridge 100 without the caps 710 is placed in the case 700, the tips of the capillaries 140 would extend into the protective sealing material. This can be viewed as a cartridge 100 container having a cartridge holder analogous to the parking stand 600 in FIG. 6. In addition, the protective case may be made to protect the capillary cartridge 100 and its tracking device 500 from electrical damage caused by electrostatic discharge using methods known in the art.

Multiple Capillary Cartridge Based CE System

FIG. 4 shows an overall perspective view of the internal components of the CE system 200 (e.g., an DNA Analyzer). FIG. 3 is an external view of the system. The CE system 200 incorporates an interface mechanism 300, in accordance with one embodiment of the present invention. The interface mechanism 300 supports a multi-channel cartridge 100 in accordance with the one embodiment of the present invention, which provides easy handling of multi-channel separation columns, and allows easy optical coupling of the detection zones to the detection optics of the CE system 200.

Figure 5:
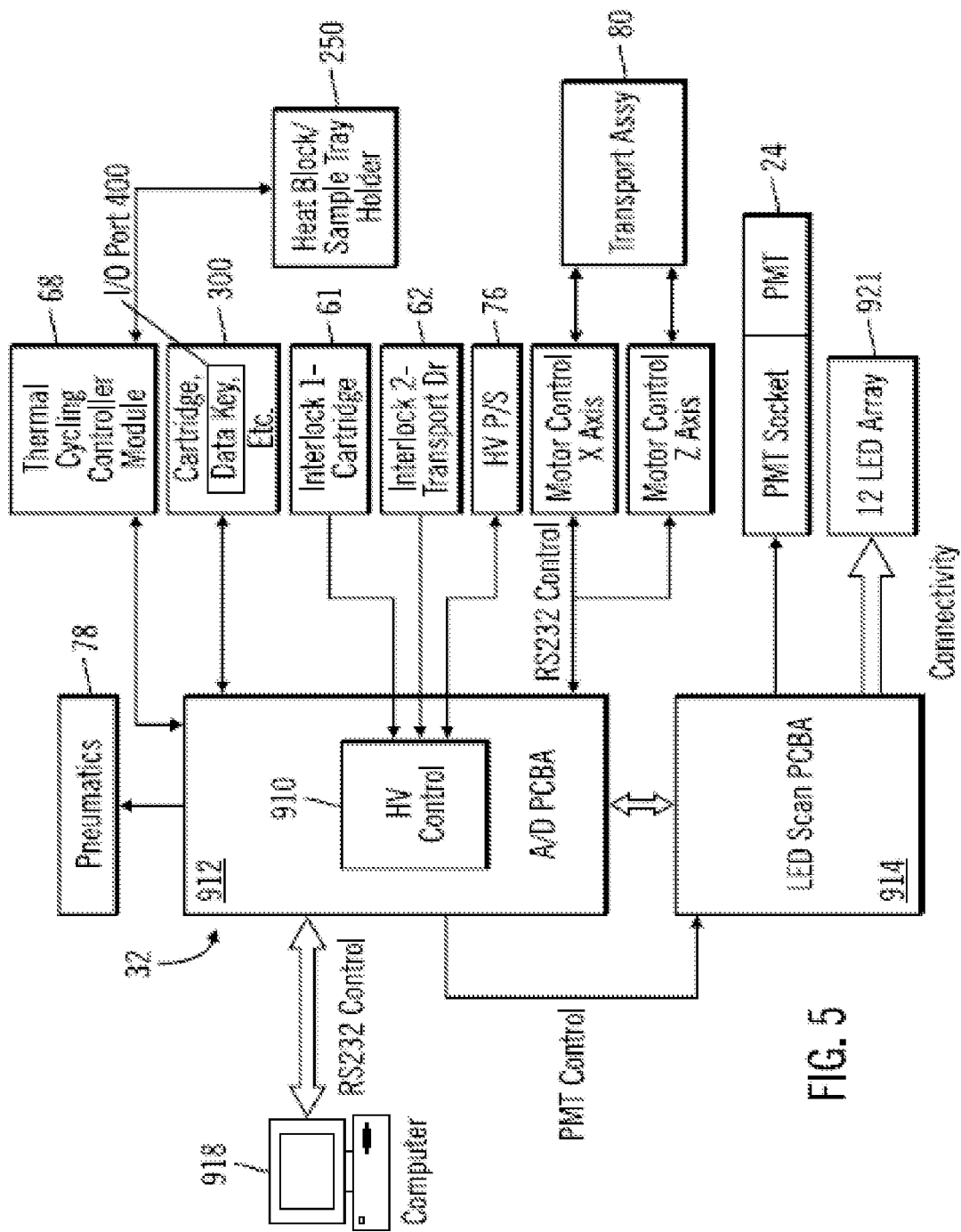
FIG. 5 is a block diagram of the control system for the bio-analysis instrument in accordance with one embodiment of the present invention.

The fully automated DNA analysis system 200 has a base 74, supporting a modular X-Z mechanism 80 having a sample tray support frame 81. The X-Z mechanism 80 supports and moves a buffer plate 70 in relation to the multi-capillary cartridge 100 supported by the interface mechanism 300, and a sample holder (e.g., a 96-well micro-titer plate 72), which may be held in an optional PCR sample preparation device 250. Specifically, the mechanism 80 comprises an X mechanism 82 for moving the support frame 81 along the X-direction relative to the cartridge 100, and a Z mechanism 83 for moving the cartridge in the Z direction relative to the support frame 81. The PCR sample preparation device 250 is controlled by a PCR thermoelectric controller 68 (FIG. 5). Additional details concerning the PCR sample preparation device 250 may be referenced to U.S. patent application Ser. No. 10/973,828, which has been fully incorporated by reference herein.

Cartridge Interface Mechanism

The cartridge interface mechanism 300 includes the I/O port 400 for reading/writing the data key 500. The I/O port 400 may include any reader/writer that is compatible with the data key 500. The data key 500 is inserted into the I/O port 400 after the cartridge 100 has been supported by the cartridge interface 300 mechanism. The reading and writing operation of the I/O key 400 is controlled by the controller 32 (described below).

Other structures and operations of the interface mechanism of the CE system 200 may be referenced to the copending U.S. patent application Ser. No. 10/823,382, which had been fully incorporated by reference herein. The cartridge interface accomplishes quick and reliable interface connections to the disposable gel contained capillary cartridge 100. These interface connections include a gas pressurization connection, high voltage connections, and precision optical connections. The interface also provides precise and repeatable mechanical positioning of the cartridge, to accurately position the components of the cartridge in relation to the support elements in the CE system 200, including positioning the capillary tips in relation to external sample or buffer reservoirs, found on 96-well titer plate, for example. Additionally, the interface provides separate electrical, optical and pneumatic connections to each separation channel, thus providing channel-to-channel isolation from cross talk both electrically and optically and insulation to the rest of the instrument from high voltage.

Detection System

U.S. Pat. No. 6,828,567, which had been fully incorporated by reference herein, is more specifically directed to the time staggered/multiplexed detection scheme that can be adopted in the CE system 200.

Control of the Automated System 200

The CE system 200 provides an integrated controller to operate the various components of the system. The operations of the CE system 200, including the interface mechanism 300 with the I/O port 400, detection system, power supply, X-Y control system, etc., are controlled by a controller 32 interfacing with an external user control interface (e.g., a PC 918), to coordinate the functions described herein.

Referring also to FIG. 5, in accordance with one embodiment of the present invention, the block diagram of the controller 32 for the CE system 200 is illustrated. The controller 32 comprises a processor as part of the A/D Board (LED Processor PCBA) 912 with CPU 910 for converting detection signals received from the detector 24 (e.g., a PMT) to corresponding digital signals, coming from LEDScan PCBA interface 914 for transferring and receiving signals to and from respective parts of the CE system 200 by instructions from the CPU 910. The A/D (LED Processor PCBA) interface 912 is coupled to the various actuators and the I/O port 400 in the interface mechanism 300 to control and connect (using the interface mechanism 300) at least high voltage power supply 76, pneumatics 78 (hidden from view in the interface mechanism 300 in FIG. 2), motor controls (X-Z sample/buffer tray) 80 and interlocks (cartridge and transport doors) 61 and 62 (details of these are not shown in the interface mechanism 300 in FIG. 2). The A/D or LED Processor PCBA 912 also controls the high-voltage power supply 76 for sample injection and electrophoresis functions of the CE system 200, a circuit 914 (LEDScan Board) for modulating the excitation radiation source (e.g., LEDs) 921 and the detector module 24 of the CE system 200. Details of the modulation of the excitation radiation source may be referenced to copending U.S. patent application Ser. No. 10/060,052, which had been fully incorporated by reference herein.

The A/D (LED Processor PCBA) 912 may be further coupled to an external personal computer 918, which in turn performs data processing or additional control function for the CE system 200, e.g., using BioCal's BioCalculator Software to control various features and functions of the automated multi-channel CE system 200 (including the optional integrated PCR sample preparation device).

The components of the controller 32, with the exception of the PC 918, may be packaged as an electronic board 64 (FIG.

4) and cooling fans 63, on board the CE system 200 and electrically coupled to the PC 918 via a serial port (not shown), or they may be part of a separate controller module outside of the CE system 200. The CPU 910 and/or the PC 918 are programmed to accomplish the various control functions and features for the CE system 200. In one embodiment, the PC 918 can be configured to provide the user control interface for the CE system 200 (e.g., user initiation of the connection sequence of the interface mechanism 300). It would be within a person skilled in the art to implement the program code given the functions and features disclosed herein. In an alternate embodiment, the controller 32 or components thereof may be incorporated as part of the PC 918.

Operation of CE System

Once the capillary cartridge 100 and the data key 500 have been mated to the instrument, the cartridge ID and the number of pre-programmed runs available from the cartridge 100 are read by the CE system 200 via the I/O port 400. The CE system 200 may employ an algorithm to determine if the capillary cartridge 100 has enough runs left to complete the process cycle before initiating the CE sequence. Otherwise, the CE system 200 may display an error message and the sequence is stopped. If it is determined that the capillary cartridge 100 has sufficient runs available, the CE sequence will start and number of runs is tracked by the CE system. At the end of the analysis, the number of remaining runs is calculated and sent to the data key 500 for storage.

The controller 32 of the instrument may be configured to "authenticate" the cartridge 100 and conduct an integrity check to determine if the particular cartridge 100 has the correct properties (e.g., gel-chemistry, number of channels/capillaries) for the particular sample analysis to be conducted. The instrument may also confirm that the user falls within the class of users permitted to use the particular cartridge. Further, the instrument may communicate/record information concerning usage of the cartridge 100 (e.g., usage history, sequence/method steps/parameter settings, patient I.D., test parameters, and perhaps test results). Such information provides an update to the stored information from the previous use of the cartridge. Further reading and writing can be controlled with respect to the data and information discussed above relating to the data key 500. The instrument may go through other checks to authenticate the test protocols the user wants to apply to the particular cartridge is proper, to determine if there are any limitations, restrictions or constraints, such as those noted before.

In operation of the CE analysis, the sample handling tray transport mechanism 80, with a 96-well plate (8×12) 72 and 70, is used to introduce the amplified DNA samples (or analytes) to each capillary 140. The X-Z transport mechanism 80 indexes a row of sample carrying wells 73 in the micro-titer plate 72 under the row of capillary tips 140 and dip the tips into the well. By applying a voltage, electrokinetic injection moves a known amount of the DNA sample to the beginning of the separation column 140. After injection, the DNA samples from sample tray 72 may be replaced with a running buffer from tray 70. Alternatively, after injection, the transport mechanism 80 may index to move a row of 12 wells 73 in the titer plate 72 containing buffer solution into position under the cartridge to replace the twelve wells containing DNA samples.

By applying high voltage across the total length of the capillary 140, separation of the DNA sample into DNA fragments is achieved. As the fragments approach the end of the capillaries 140 and enter into the detection zone, the excitation light energy (e.g., from twelve LEDs delivered by optical fibers) is directed at the detection zone, illuminating the migrating DNA fragments. The detection scheme may be in a time-staggered manner as disclosed in copending U.S. application Ser. No. 10/060,052.

To prepare for the next run with a different sample, the old gel from the previous run is purged from the capillaries by pressuring the reservoir to refill the capillaries with fresh gel. The trays 70 and/or 72 carry cleaning solutions, waste collection, and samples. The purged gel is collected by one of the trays 70 and 72 by positioning the tips of the capillaries at a row of waste collecting wells in one of the trays. The tips of the capillaries may be cleaned with water or a cleaning solution by positioning and dipping the tips of the capillaries in such solution in the appropriate tray wells. When the capillaries are refilled and ready for the next run, the tips of the capillary are dipped into the samples by repositioning the tray 72. The above mentioned sequence of process may be programmed as one of the automated functions of the controller 32. The interface mechanism 300 provides the interfacing of support elements in the CE system 200 to the cartridge, such as high voltage, gas pressure, LED radiation source, and detection optics, as described above.

After the analysis has been completed, the cartridge 100 may be stored on the parking stand 600, or in the protective case 700, or the capillaries capped with protective caps 710. The cartridge 100 may be retrieved and reused when needed for another analysis at a later time or date. If a different run condition is contemplated, a different cartridge having different attributes and properties may be used instead. The data key mechanism of the present invention would automatically keep track of the usage of the different interchangeable cartridges, without requiring the user to manually keep track of such.

While the invention has been particularly shown and described with reference to the preferred embodiments, it will be understood by those skilled in the art that various changes in form and detail may be made without departing from the spirit, scope, and teaching of the invention.

Although some of the embodiments describe a tracking mechanism and an I/O port that consist of a Serial Memory Key and a card reader/writer, the invention may also use other types of erasable memory such as a Multi-Media Card or a Compact Flash card. In an alternate embodiment, the tracking mechanism may use a wireless transmitters/receivers or an optical means such as an optical disc and an optical disc reader/recorder. Such tracking mechanism may be activated when the CE instrument is not involved in a high-voltage processing step to ensure quality data link. Still in another embodiment, the tracking mechanism may consist of a smart label and an optical reader and printer. For example, the smart label containing a bar code and a series of symbols that can be optically read by a scanner on the CE system to extract the ID and number of run completed by the cartridge. After a subsequent analysis cycle, a thermal printer or inkjet printer on the CE system can modify the smart label to reflect the current number of runs completed by the cartridge.

While the tracking device is described in some embodiments as being attached to the cartridge by a cord, it can be appreciated that the tracking device can be attached to the cartridge by another type of tethered connection such as a chain. Alternately, the tracking device can be connected to the cartridge via a rigid connection such as a flange or an extension arm of a fixed length so that the cartridge and the tracking device can mate with the cartridge-mating interface and the I/O port in one movement.

The automated system 200 may be configured to conduct other types of analysis different or in addition to CE separation and analysis. For example, for protein or bioagent detection, carbohydrates or immunoassays combined with the micro-fluidic electrophoresis system could also be used. Protein extract from cultures is used for immunoassays. The amplification signals via interaction of antigen and antibody conjugated fluorescence dye is automatically applied to a multi-channel cartridge for high-resolution detection within several minutes.

Although some of the embodiments describe a communication process that involves a read/write capability between the bio-analysis system and the tracking device, it can be appreciated that the communication process may involve a read-only process. For example, the bio-analysis system can read the cartridge ID and send this information to a central remote database prior to starting a bio-analysis sequence. After the subsequent bio-analysis cycle is completed, the bio-system can send updates to the central database instead of sending them to the tracking device for storage.

Interface mechanisms may be adapted to receive capillary cartridges of other structural designs. A person skilled in the art will recognize that the instrument incorporating the essence of this invention can also be used for bio-molecular analysis other than DNA analysis. For example, by altering the separation gel or buffer, the instrument can also be modified to analyze biomolecules like proteins, carbohydrates, and lipids.

By way of example and not limitation, the detection scheme of the present invention is described in connection with capillary electrophoresis and radiation induced fluorescence detection. It is understood that the present invention is also applicable to detection of analytes separated based on bio-separation phenomenon other than electrophoresis, and detection of radiation emissions other than fluorescence emissions, including other types of emissive radiation, such as phosphorescence, luminescence and chemiluminescence, as well as UV and Visible absorbance based detection.

Furthermore, while the separation channels in the described embodiments are defined by cylindrical columns or tubes, it is understood that the concepts of the present invention is equally applicable to separation channels defined by channels, for example micro-channels (such as square, rectangular or essentially semicircular cross sections) defined by etching or micro-machining in a substrate (micro-fluidics type devices or bio-chips).

The transport mechanism can be configured to move the trays in a horizontal plane, and an additional transport mechanism may be provided to move the trays vertically to access the trays.

Accordingly, the disclosed invention is to be considered merely as illustrative and limited in scope only as specified in the appended claims.

We claim:

1. A cartridge system for bio-analysis, comprising:
a cartridge having a body defining at least a channel for passage of a sample for analysis, wherein the cartridge comprises a body, and the channel comprises a capillary column supported by the body, and wherein the cartridge comprises a structure designed for capillary electrophoresis separation of a sample in the capillary column; and
a data key associated with the cartridge, comprising a rewritable memory storing data relating to attributes of the cartridge, which data is readable by an external reader, wherein the data key is isolated from the body of the cartridge at an extended distance.

2. The cartridge system as in claim 1, wherein the data key is coupled to the cartridge by a tether, extending the data key at a distance from the body of the cartridge.

3. The cartridge system as in claim 1, wherein the data key comprises a non-volatile rewritable memory for storing data, including updatable data relating to usage of the cartridge.

4. The cartridge system as in claim 1, wherein the data key stores data relating to at least one of the following attributes: model number, serial number, number of channels, size of channels, medium of channels, designated patient or subject ID, date of manufacturing, chemistry lot number, designated user restrictions, designed usage limitation, restriction or constraint, expiration date, maximum service voltage, maximum number of runs, maximum hours of use, chemistry compatibility, and instrument compatibility.

5. The cartridge system as in claim 4, wherein the data key further stores data relating to at least one of the following updatable data relating to usage: cumulative number of runs, types of runs, running conditions and parameters, dates of use, cumulative run time, run protocols, separate run times, run IDs, patient or subject IDs, user IDs, applied run voltage, instrument system ID's for each run.

6. The cartridge system as in claim 1, wherein the cartridge is characterized by at least one of the following: portable, recyclable, reusable and interchangeable with other cartridges having different types of channels.

7. The cartridge system as in claim 1, wherein the structure includes an electrode for applying a high voltage across the capillary column for capillary electrophoresis.

8. The cartridge system as in claim 1, wherein the cartridge comprises a body, and the channel comprises a capillary column containing a gel supported by the body terminating at one end, wherein the stand comprises a sealing material, and wherein the cartridge is removably support on the stand with respect to the sealing material, such that the terminating end of the capillary extends into the sealing material.

9. The cartridge system as in claim 1, wherein the cartridge comprises a body, and the channel comprises a capillary column containing a gel supported by the body terminating at one end, the cartridge system further comprising a thin-walled capsule containing a sealing material, and wherein the terminating end of the capillary is inserted into the capsule to seal the terminating end.

10. A bio-analysis system, comprising:
a base;
a cartridge system as in claim 1;
a cartridge interface supported on the base, interfacing with the cartridge system; and
a controller operatively coupled to the cartridge interface to control operations of the cartridge interface.

11. The bio-analysis system as in claim 10, wherein the cartridge interface comprises a data interface to operatively couple to the data key.

12. The bio-analysis system as in claim 11, wherein the data interface comprises an I/O port that reads data from the data key.

13. The bio-analysis system as in claim 12, wherein the I/O port further writes data to the data key.

14. The bio-analysis system as in claim 10, wherein the controller controls the cartridge interface to effect electrophoresis separation of a sample in the channel.

15. The bio-separation system as in claim 11, wherein the data key communicates with the cartridge interface via the data interface, concerning data relating to at least one of the following attributes: model number, serial number, number of channels, size of channels, medium of channels, designated patient or subject ID, date of manufacturing, chemistry lot number, designated user restrictions, designed usage limitation, restriction or constraint, expiration date, maximum service voltage, maximum number of runs, maximum hours of use, chemistry compatibility, and instrument compatibility.

16. The bio-separation system as in claim 11, wherein the data key communicates with the cartridge interface via the data interface, concerning data relating to at least one of the following updatable data relating to usage: cumulative number of runs, types of runs, running conditions and parameters, dates of use, cumulative run time, run protocols, separate run times, run IDs, patient or subject IDs, user IDs, applied run voltage, instrument system ID's for each run.

* * * * *